(12) United States Patent
Metysek et al.

(10) Patent No.: US 10,105,504 B2
(45) Date of Patent: Oct. 23, 2018

(54) EAP-DRIVEN AIR PUMP FOR PATIENT INTERFACES

(71) Applicant: KONINKLIJKE PHILIPS N.V., Eindhoven (NL)

(72) Inventors: Mark Metysek, Hofheim (DE); Cornelis Petrus Hendriks, Eindhoven (NL); Roland Alexander Van De Molengraaf, Geldrop (NL); Matthew John Lawrenson, Bussigny-Pres-de-Lausanne (CH); Julian Charles Nolan, Pully (CH); Melanie Jane Windridge, Bucks (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 652 days.

(21) Appl. No.: 14/652,799

(22) PCT Filed: Dec. 16, 2013

(86) PCT No.: PCT/IB2013/060990
§ 371 (c)(1),
(2) Date: Jun. 17, 2015

(87) PCT Pub. No.: WO2014/097119
PCT Pub. Date: Jun. 26, 2014

(65) Prior Publication Data
US 2015/0320958 A1 Nov. 12, 2015

Related U.S. Application Data

(60) Provisional application No. 61/738,579, filed on Dec. 18, 2012.

(51) Int. Cl.
*A61M 16/06* (2006.01)
*A61M 16/00* (2006.01)
(Continued)

(52) U.S. Cl.
CPC ........ *A61M 16/0057* (2013.01); *A61M 16/06* (2013.01); *A61M 16/20* (2013.01);
(Continued)

(58) Field of Classification Search
CPC .. A61M 16/0057; A61M 16/06; A61M 16/20; A61M 16/201; A61M 16/202;
(Continued)

(56) References Cited

U.S. PATENT DOCUMENTS 5,850,833 A 12/1998 Kotliar
6,071,088 A 6/2000 Bishop
(Continued)

FOREIGN PATENT DOCUMENTS

CN 1655839 A 8/2005
CN 1867372 A 11/2006
(Continued)

OTHER PUBLICATIONS

Artificial Muscle Inc., July 7, 2011 http://www.artificialmuscle.com/products/bayfol-reflex.php?q=products/reflex-products.php.

*Primary Examiner* — Lynne Anderson
*Assistant Examiner* — Joseph D Boecker
(74) *Attorney, Agent, or Firm* — Michael W. Haas

(57) ABSTRACT

The present invention relates to a gas supply system (10) for a patient interface (30) for supplying a flow of pressurized gas to a subject (50), an according patient interface (30) with such a gas supply system (10) and a therapy device with such a gas supply system. The gas supply systems according to the present invention comprise a pump device (55) that has at least one membrane (58) for pumping actuation. This membrane (58) is actuated via an electro-active polymer material (60).

13 Claims, 10 Drawing Sheets

(51) Int. Cl.
   *A61M 16/20* (2006.01)
   *F04B 45/047* (2006.01)

(52) U.S. Cl.
   CPC ....... *F04B 45/047* (2013.01); *A61M 16/0633* (2014.02); *A61M 2205/0283* (2013.01); *A61M 2205/3334* (2013.01); *A61M 2205/42* (2013.01); *A61M 2209/088* (2013.01)

(58) Field of Classification Search
   CPC ........ A61M 16/203; A61M 2205/0272; A61M 2205/0283; A61M 2205/3334; A61M 2205/3344; A61M 2205/42; A61M 2209/088; A61M 16/00; A61M 16/0003; A61M 16/021; A61M 16/022; A61M 16/0611; A61M 16/0622; A61M 16/0633; F04B 45/047
   See application file for complete search history.

(56) References Cited

U.S. PATENT DOCUMENTS

| | | | |
|---|---|---|---|
| 7,362,032 B2 | 4/2008 | Pelrine | |
| 7,397,166 B1 | 7/2008 | Morgan | |
| 9,925,347 B2 * | 3/2018 | Van De Molengraaf | A61M 16/0605 |
| 2003/0117044 A1 * | 6/2003 | Urano | F04B 43/0054 310/367 |
| 2003/0214199 A1 * | 11/2003 | Heim | F04B 35/045 310/309 |
| 2004/0008853 A1 * | 1/2004 | Pelrine | A61M 5/142 381/191 |
| 2004/0068220 A1 | 4/2004 | Couvillon, Jr. | |
| 2004/0068224 A1 | 4/2004 | Couvillon, Jr. | |
| 2005/0252513 A1 | 11/2005 | Dingley | |
| 2006/0096596 A1 * | 5/2006 | Occhialini | A61M 16/0057 128/204.18 |
| 2007/0128059 A1 | 6/2007 | Bagwell | |
| 2008/0083412 A1 | 4/2008 | Henry | |
| 2009/0078257 A1 | 3/2009 | Bhat | |
| 2009/0320842 A1 * | 12/2009 | Doherty | A61M 16/06 128/204.21 |
| 2010/0037896 A1 | 2/2010 | Mashak | |
| 2010/0109486 A1 | 5/2010 | Polyakov | |
| 2010/0221124 A1 | 9/2010 | Ikushima | |
| 2011/0120456 A1 | 5/2011 | Immel | |
| 2011/0126832 A1 | 6/2011 | Winter | |
| 2011/0189027 A1 | 8/2011 | Hansen | |
| 2012/0192869 A1 | 8/2012 | Hayek | |
| 2013/0071273 A1 * | 3/2013 | Locke | F04B 43/046 417/480 |
| 2014/0166007 A1 | 6/2014 | Bordewick | |
| 2014/0261425 A1 * | 9/2014 | Connor | A61M 16/022 128/204.23 |
| 2015/0020810 A1 * | 1/2015 | Stupak | A61M 16/0666 128/205.19 |
| 2016/0199607 A1 * | 7/2016 | Kenyon | A61M 16/0066 128/204.23 |

FOREIGN PATENT DOCUMENTS

| | | |
|---|---|---|
| CN | 101466428 A | 6/2009 |
| CN | 101658703 A | 3/2010 |
| EP | 1323925 A2 | 7/2003 |
| EP | 1655052 A2 | 5/2006 |
| WO | WO9637176 A1 | 11/1996 |
| WO | WO2010033926 A1 | 3/2010 |
| WO | WO2013183018 A1 | 12/2013 |

* cited by examiner

EAP-DRIVEN AIR PUMP FOR PATIENT
INTERFACES

CROSS-REFERENCE TO RELATED
APPLICATIONS

This patent application claims the priority benefit under 35 U.S.C. § 371 of International Patent Application No. PCT/IB2013/060990, filed Dec. 16, 2013, which claims the priority benefit under 35 U.S.C. § 119(e) of U.S. Provisional Application No. 61/738,579 filed on Dec. 18, 2012, the contents of which are herein incorporated by reference.

FIELD OF THE INVENTION

The present invention relates to a gas supply system, a patient interface and a therapy device for providing a controlled flow of pressurized gas to a subject using a pump device with an electro-active polymer material.

BACKGROUND OF THE INVENTION

Patient interfaces, such as masks for covering the mouth and/or nose, are used for delivering gas to a subject. Such gases, like air, cleaned air, oxygen, or any modification of the latter, are submitted to the subject via the patient interface in a pressurized or unpressurized way.

For several chronic disorders and diseases, a long-term attachment of such a patient interface to a subject is necessary or at least advisable.

One non-limiting example for such a disease is obstructive sleep apnoea or obstructive sleep apnoea syndrome (OSA). OSA is usually caused by an obstruction of the upper airway. It is characterized by repetitive pauses in breathing during sleep and is usually associated with a reduction in blood oxygen saturation. These pauses in breathing, called apnoeas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway in order to keep it open. Positive air pressure is thus provided to a subject through a hose connected to a patient interface or respiratory interface, such as a face mask, that is worn by the subject. The afore-mentioned long-term use of the patient interface is the result, since the wearing of the patient interface takes place during the sleeping time of the subject.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both,
total face masks, which fit over the whole face, and
nasal pillows, which are regarded as masks as well within the scope of the present invention and which consist of small nasal inserts that deliver the gas directly to the nasal passages.

The patient interface is usually positioned on the subject's head using some kind of headgear.

The afore-mentioned long term use of the patient interfaces in order to achieve an envisaged therapy result during night often causes discomfort for the patient or a subject. This is due to the afore-mentioned hose connecting the patient interface to an external therapy device which limits the patient in his/her movement freedom and disturbs the sleep of the patient or subject, e.g. by a limited length of the hose or by the hose getting under the patient because of the usual movements during sleep. This therapy device includes a pump device which is controlled based on certain parameters and the therapeutic need. Since the mentioned therapy device is normally disposed stationary beside the bed the subject or patient is permanently connected to this stationary device via the hose during night which causes the afore-mentioned discomfort.

Further, the currently existing therapy devices have a size comparable to two larger books and an according high weight which results in further discomfort if the subject or patient is not staying at the same place for sleeping, e.g. if the subject wants or needs to travel.

SUMMARY OF THE INVENTION

It is an object of the present invention to provide a gas supply system for a patient interface, an according patient interface and a hand-held therapy device that reduces the discomfort for a subject wearing such a patient interface overnight and also facilitates an easier portability of an according therapy device.

According to an aspect of the present invention, a gas supply system for a patient interface for supplying a flow of pressurized gas to a subject is provided, with
at least one pump device, comprising:
at least one membrane with an electro-active polymer material, and
at least one valve; and
a controller, for controlling the at least one pump device,
wherein the at least one membrane is arranged such that it is in operative communication with at least one closed volume and is further designed for altering the size of the at least one closed volume based on actuation by the electro-active polymer material in a periodic way resulting in a flow of pressurized gas.

According to another aspect of the present invention a patient interface for supplying a flow of pressurized gas to a subject is provided, with:
an interfacing portion that gets in contact with the subject, and
a gas supply system according to the present invention.

According to another aspect of the present invention, a therapy device for providing a controlled flow of pressurized gas to a patient interface is provided, with a gas supply system according to the present invention.

The term "gas" as used within the context of the present invention is to be understood as encompassing gases that can be applied or provided to a living subject, like but not limited to air, cleaned air, oxygen, or any modifications of the latter.

The term "gas source" as used within the context of the present invention is to be understood as encompassing any suitable source for the afore-mentioned gas, like but not limited to gas bottles, gas lines, e.g. leading to gas tanks, ambient or surrounding air etc.

The term "electro-active polymer material" as used within the context of the present invention is to be understood as a polymer material that is able to change its properties, preferably its shape, more preferably its thickness and/or length due to the application of an electric field. One non-limiting example for such electro-active polymer materials are dielectric electro-active polymers (DEAP).

The afore-mentioned controller can be realized as any suitable electronic device comprising for example a processor, memory, etc. or a micro-controller. Therein, one controller may control all pump devices or all membranes of an according gas supply system. Further, it is possible that every pump device or even every membrane has an individual controller, and that in such an arrangement a connection of the controllers is possible in order to achieve a coordinated movement of the membranes or work of the pump devices. This can either be done by connecting the individual controllers with each other or by having one or more main controllers controlling the individual controllers. Within the context of the present invention and in the following description, a reference to "the controller" is to be understood as encompassing all the afore-mentioned variations.

Preferably, the controller is designed to control the at least one pump device to supply a controlled pressurized flow of gas to the subject via the patient interface. More preferably, the controller is further designed to control the at least one pump device such that it provides this controlled pressurized flow in a way suitable for achieving an envisaged therapeutic effect on the subject based on predetermined and/or determined parameters.

Devices commonly used today for a CPAP therapy, for example, have an external therapy device that generates the pressurized flow of gas by one or more blowers. These devices are therefore limited in their design, size and weight. By including and using a pump device with an electro-active polymer material as an actuator in order to achieve the desired flow of pressurized gas the overall device, that is to say the gas supply system either included in the patient interface or in the therapy device, gets more flexible with respect to its design and form. This means that the form of the overall device can be accommodated to a desired shape and that the device can be integrated more easily in other structures, like but not limiting to patient interfaces.

This allows for including the pump device directly in the patient interface, making a hose connection to a stationary system beside a bed unnecessary and thereby increasing the comfort for the subject. Further the gas supply system may comprise a reduced size and may be more lightweight than the known therapy devices. Such a smaller and lightweight design gives a possibility for easy transportation of the whole patient interface system including the therapy device, either by including the pump device and the therapy device in the patient interface, as mentioned before, or by providing a hand-held, i.e. easy portable, therapy device. For this, the controller is designed to control the pump device, e.g. the at least one membrane actuated by the electro-active polymer material in such a way that a controlled flow of the pressurized gas results. In this context, controlled flow means such a flow that is biologically acceptable for a living subject, that is to say, does not harm the subject and preferably leads to an envisaged therapeutic effect. Characteristics of these controlled flow include, but are not limited too, pressure and volume per time (flow rate) as well as the respective time dependent values of these characteristics. To achieve this, the control by the controller is preferably based on predetermined and/or determined parameters. These parameters can be predetermined parameters like thresholds for pressure or volume per time, both upper and lower thresholds, as well as determined parameters that are read from input interfaces, like but not limiting to keyboards, sensors or the like. All parameters may be based on the desired therapeutic effect and biological or medical data of the subject, like but not limiting to weight, height, lung volume etc. Further the determined parameters can also be determined in real time, that is to say, during operation of the device based for example on sensors reading the breathing frequency of the subject, its pulse, the pressure within the system or the like.

Aside from the pump device comprising at least one valve, it is further preferred that the pump device comprises at least two valves. This way, better results for pressure and flow rate, and therefore efficiency, can be achieved.

Preferred embodiments of the invention are defined in the dependent claims. It should be understood that the claimed patient interfaces, the claimed therapy devices and the claimed uses can have similar preferred embodiments as the claimed gas supply system and as defined in the corresponding dependent device claims.

According to an embodiment of the gas supply system of the present invention, the gas supply system comprises at least two pump devices. These at least two pump devices can be arranged in primarily two different ways, either parallel with respect to each other or serial. In cases where the gas supply system comprises more than two pump devices the arrangement of these at least three pump devices may be any combination of the afore-mentioned parallel and the serial arrangement. For example, all three pump devices may be arranged with respect to each other in a parallel or in a serial arrangement, or also a combination of two of the pump devices in a parallel arrangement with the third pump device arranged in serial to the afore-mentioned combination of two is possible. A parallel arrangement, that is to say, an arrangement where especially the gas output of the at least two pump devices is combined in the end, gives the possibility of an increased flow compared to a single pump device. On the other hand, arranging the pump devices in serial, that is arranging the output of a first pump device at the input of a second pump device provides the possibility of increasing the overall output pressure. It goes without saying that any combination in cases with at least three pump devices may provide both afore-mentioned effects.

According to another embodiment of the gas supply system of the present invention, the gas supply system comprises at least two membranes each membrane generating a force due to its movement upon actuation, wherein the membranes are arranged in the gas supply system such that the sum of forces of the membranes is lower than each individual force of the membranes. In such an arrangement the forces resulting from the actuation of the membranes by the electro-active polymer materials, which are periodical and induce a vibration because of the frequencies of these periodical movements, can be reduced, preferably reduced to less than 10% of the individual forces of the respective membranes, or more preferably cancelled out. This is beneficial since the originally resulting forces act, depending on the realization of the gas supply system, on the subject wearing the patient interface or at least on the therapy device resulting in either movement or at least a disturbing vibrational sound. Both effects increase a discomfort of the subject and should preferably be avoided. This can be done based on the present embodiment by arranging the membranes in the gas supply system differently, that is to say, with their direction of actuation in different directions such that one force resulting from the actuation of one membrane is reduced or preferably eliminated by the force resulting from the actuation of another membrane. This can preferably lead to a device, e.g. a patient interface or a therapy device that does not show a vibration detectable for a subject. This of course increases the comfort for the subject.

For such an arrangement the controller is further preferably designed to control the membranes, i.e. the electro-active polymer materials, in such a way that the movements of membranes occur concerted. This concerted movement is realized by a coordinated actuation with respect to the time of actuation and also with respect to the magnitude of the actuation, e.g. the deflection, of the respective membranes. Thereby, not only setups with two but also with three or more membranes may be realized according to this embodiment resulting in devices that show no significant vibration due to a concerted or coordinated control of the membranes. Therein, each membrane may be addressed by the controller individually and in a way that also leads to different magnitudes of actuation of the individual membranes with respect to each other in order to reduce or cancel out the forces and accordingly the vibration. Aside from controlling every membrane in this respect it is also possible that at least one membrane has an independent actuation, that is to say, independent with respect to the resulting forces but not necessarily independent of the aforementioned parameters, and the remaining membranes being controlled in order to reduce, preferably reduce to less than 10% of the individual forces, or more preferably cancel out the overall force of the device and thereby the vibration According to another embodiment of the gas supply system of the present invention, the at least one pump device comprises at least two membranes, each membrane comprising at least one electro-active polymer material. With such an arrangement the efficiency of an individual pump device can be increased due to at least two membranes being responsible for the change in the volume size. This may lead to better and higher flow rates or also to increased pressures if desired.

According to another embodiment of the gas supply system of the present invention, the pump device comprises the closed volume, and the membranes are arranged on opposite sides on the closed volume. With such an arrangement the reduction or preferably cancellation of the forces, as mentioned before, may be realized within a single pump device. Further, due to at least the two membranes being responsible for the change in the size of the closed volume within the pump device, the actuation of those membranes may be coordinated such that the output, that is to say the flow and the pressure, of the pump device is improved while at the same time a reduction or cancellation of the forces and therefore of any vibration can be achieved.

According to another embodiment of the gas supply system of the present invention, the at least one valve is an active valve. With an active valve, also called controllable valve, not even the control of the pump devices with respect to their membranes is possible by the controller but also a control of the opening and closing of the valves with respect to time and also in their extend can be realized. This is done preferably by the controller. Aside from the positive effect of having a further controllable member, controllable valves are further beneficial since they allow for higher frequencies of opening and closing than uncontrolled valves. This allows for coordination of the opening and closing of the valve(s) with the actuation of the membrane(s). Wherein in pump devices with passive valves a delayed valve response during the switch from the suction to the exhaustion step (or from the exhaustion to the suction step) may result in unwanted flows out of the pump device (or in the pump device) this may be avoided by active/controllable valves since an opening and closing of the valves can be realized faster and concerted with the operation of the pump device. This increases the overall efficiency of the pump device and therefore of the gas supply system.

According to another embodiment of the gas supply system of the present invention, the at least one valve is actuated by an electro-active polymer material. By using electro-active polymer materials for actuation of the valves an active arrangement of the valves by using small actuators, compared to common mechanical arrangements, is possible. Further, such resulting valves are also lightweight which further contributes to achieving light weight patient interfaces or therapy devices as mentioned before.

According to another embodiment of the gas supply system of the present invention, an actuation of the at least one valve is synchronized with the actuation of the at least one membrane. Due to this synchronization and accordingly coordination of the actuation of those elements of the pump device, i.e. the valve(s) and the membrane(s), the efficiency of the pump device can be optimized and the actuation via the membrane(s) driven by the electro-active polymer material can be in a way that is most effective.

According to another embodiment of the gas supply system of the present invention, the at least one valve is arranged in the at least one membrane. Such an arrangement puts all the afore-mentioned movable parts, i.e. the membrane(s) and the valve(s), in one location. Additional openings or attachments for including a valve in the side of a housing of the pump device or at least located besides the membrane(s) are not necessary. This is especially feasible for an integration into a device like the patient interface.

According to another embodiment of the gas supply system of the present invention, the pump device comprises:
at least one inlet valve and
at least one outlet valve. Having separate valves for receiving and providing the gas in a gas flow results in a generation of a pressurized gas flow that can be controlled more easily and that also allows higher pressures. This is especially beneficial if the pump device is self-contained.

According to an embodiment of the patient interface according to the present invention, the gas supply system is an integral part of the patient interface. By including the gas supply system in the patient interface such that it is an integral part, the overall patient interface becomes a very compact and comfortable device. Therein the gas supply system features may be distributed over the whole patient interface, including but not limited to a mask or the like, a forehead support, hose connectors, a head cap, etc. Thereby an optimized effectivity can be achieved for the whole gas provision while at the same time the parts and features of the gas supply system can be arranged in the patient interface in such a way that the distribution of the single weights of the element of the gas supply system can be as even as possible. This leads again to a more comfortable and improved varying experience for the subject.

According to another embodiment of the patient interface of the present invention the interfacing portion comprises a mask having an outer shell, and the at least one membrane of the pump device is arranged in the shell of the mask. This way the gas supply system is directly included in the patient interface. For such a purpose the membrane(s) can be arranged on/in the patient interface on any desired and suitable position that preferably has a shape allowing an optimal fit of the respective membrane in this position. As a consequence, the design of such a patient interface according to the present invention can be very flexible and allows that the respective position(s) of the membrane(s) can be chosen such that an optimal and effective pressurized gas flow is achieved while at the same time the weight distribution and in the consequence the comfort for the patient is preferably improved. This way it can be avoided to attach bulky and/or heavy parts on the outside of the patient interface which would again lead to discomfort for the patient/subject. Accordingly, having less attachments and elements on the outside of the patient interface as mentioned before increases the comfort for the subject as well. The membrane can be disposed and shaped on the patient interface in any desired and way that is technically possible. As a result one or more single membranes can be included in the shell of the patient interface mask, preferably in a manner wherein a plurality of membranes are arranged opposite with respect to each other in order to reduce or cancel out the actuating forces, or a single membrane or a plurality of membranes can be arranged for example close to the rim of the mask in a loop-like or circular fashion.

According to another aspect of the present invention, a use of a gas supply system according to the present invention in a patient interface is provided.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
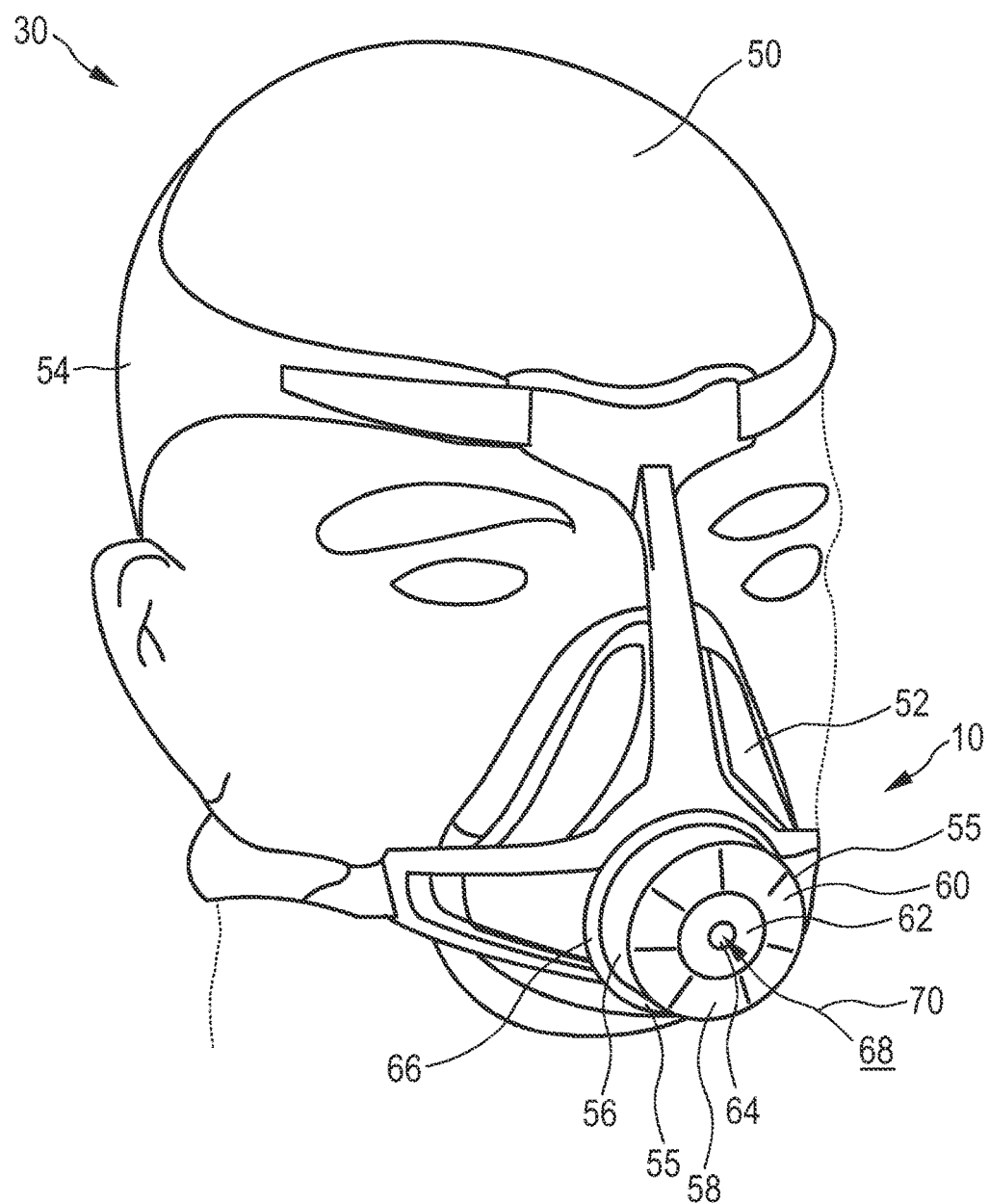
FIG. 1 shows a schematic illustration of a patient interface with a gas supply system according to the present invention worn by a subject.

Embodiments of a gas supply system according to the present invention are shown throughout and described with the help of FIGS. 1 through 15 and are designated in their entirety by the reference numerals 10, 12, 14, 16, 18, 20, 22 and 24, respectively. Further, embodiments of a patient interface according to the present invention comprising a gas supply system according to the present invention are shown throughout and described with the help of FIGS. 1 through 4, 12, 13 and 14 and are designated in their entirety by the reference numerals 30, 32, 34, 36, 38, 40 and 42, respectively. Furthermore, embodiments of therapy devices according to the present invention comprising a gas supply system according to the present invention are shown in and described with the help of FIGS. 14 and 15 and are designated in their entirety by the reference numerals 46 and 48.

Gas supply system 10 shown in FIG. 1 is directly arranged on and therefore a part of the patient interface 30. The patient interface 30 is arranged on a subject 50 in order to provide a pressurized flow of gas to the subject 50, for example as a treatment of OSA. The patient interface comprises a full-face mask 52 and a head gear 54. Primarily the mask 52 acts in this case (as well as in the following cases) as an interfacing portion to the subject 50.

Figure 5:
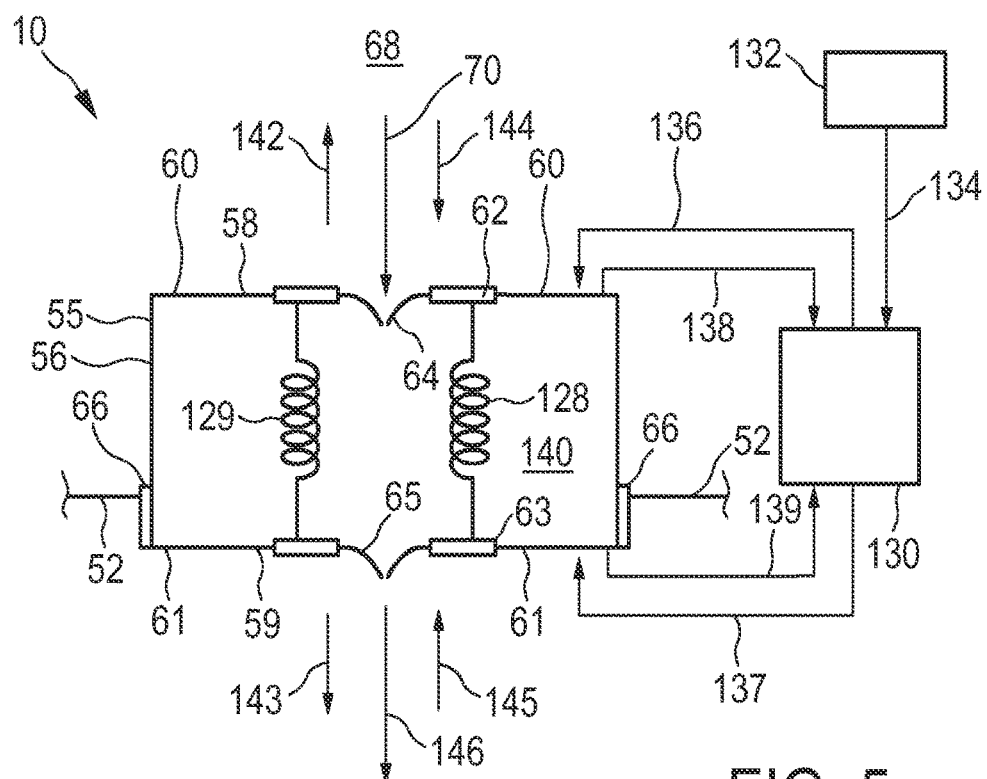
FIG. 5 shows a schematic sectional view through a pump device of a gas supply system according to the present invention.

In the present embodiment the gas supply system 10 is arranged on the part of the mask 52 where a connector for a hose is usually disposed. Gas supply system 12 comprises a pump device 55 with a housing 56 which comprises a membrane 58 on a distal end and a proximal membrane 59 (FIG. 5). The membranes 58 and 59 comprise a respective electro-active polymer material 60 (and 61, FIG. 5) and an inner plate 62 (and 63, FIG. 5). The inner plate 62 (and 63) comprises a valve 64 (and 65, FIG. 5).

The housing 56 is arranged on the mask 52 via a support element 66. This support element 66 is designed as a compressible material and acts as a connecting element between the housing 56 and the mask 52. Due to the compressibility of the support element 66 any vibrations that occur due to the actuation of the membranes 58 and 59 will be absorbed and thereby not transferred via the mask 52 to the subject 50.

Aside from such a passive absorption of vibrations by the compressible support element 66, the support element 66, as well as any other support element described herein and used for reducing the vibrations transmitted to a subject, may be designed to actively compensate any vibrations generated by the gas supply systems. A non-limiting example for such an active support element 66 may comprise electro-active polymer materials. These electro-active polymer materials may be actuated in a way that they also generate vibrations that may superimpose with the vibrations generated by the pump devices, for example, and thereby reduce or preferably cancel out the overall vibration(s) of the gas supply system.

This may for example be realized by controlling the actuation of the electro-active polymer materials of the support element(s) by a controller which also controls the actuation of the membranes. Thereby the actuation of these electro-active polymer materials may be coordinated with the actuation of the membranes in the pump devices. This leads to an effective active compensation/reduction of vibration(s).

During operation of the gas supply system 10 the membranes 58 and 59 are actuated by the electro-active polymer material 60, as will be explained later on, and ambient air 68 is pumped into the housing 56 via the valve 64. This is indicated by an arrow 70. From there the air 68 is further transported resulting in a pressurized flow of gas, i.e. ambient air 68, in the mask 52 and thereby to the subject 50. This results in a pressurized flow of ambient air 68 to the subject 50 which is for example desired as a treatment and for achieving a therapeutic effect for OSA.

Figure 2:
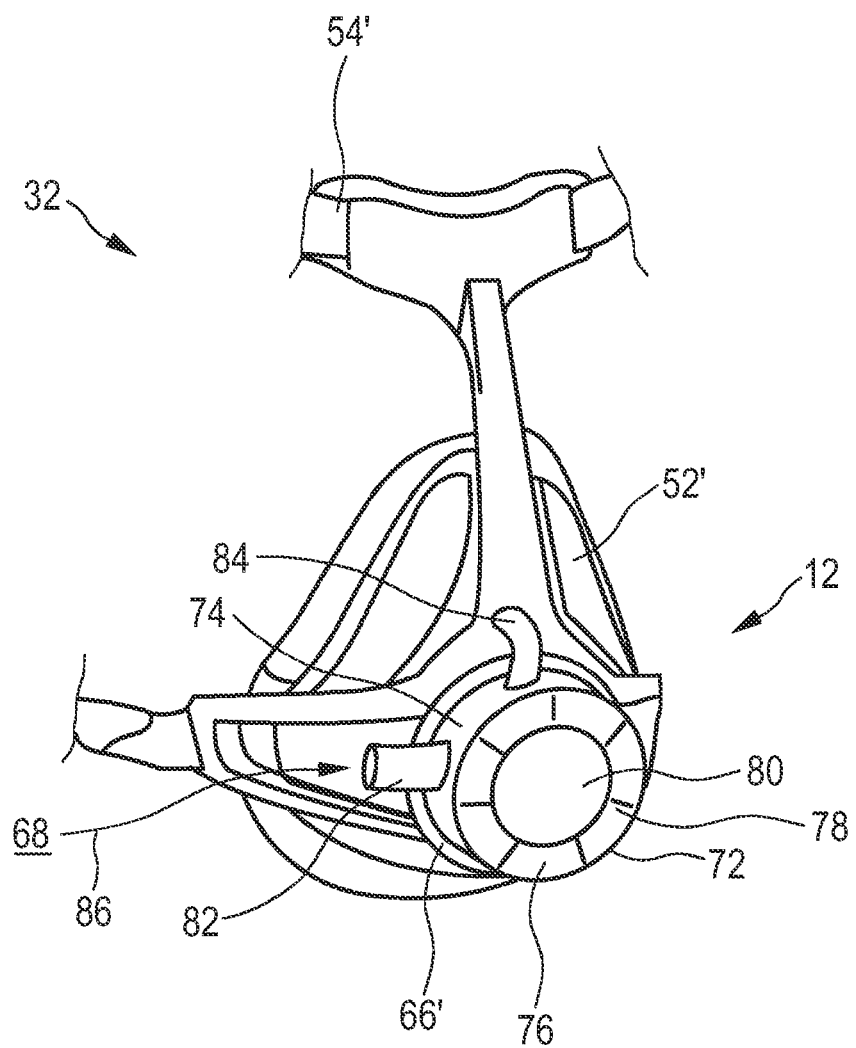
FIG. 2 shows another exemplary embodiment of a gas supply system on a patient interface according to the present invention.

FIG. 2 shows the gas supply system 12 which is arranged on and thereby part of the patient interface 32.

The patient interface 32 is similar to the patient interface 30. Therefore similar or identical parts are designated by the same reference numeral only differing in a prime (').

The gas supply system 12 comprises a pump device 72 with a housing 74. Housing 74 comprises also a membrane 76 on its distal end and another membrane on its proximal end (not shown). Membrane 76 comprises an electro-active polymer material 60 and a stiff inner plate 80. The proximal membrane comprises the same configuration. In contrast to the embodiment of the gas supply system 10 the housing 74 of the gas supply system 12 comprises further a gas inlet 82 and a gas outlet 84. Whereas the gas inlet 82 is open towards the external environment so that ambient air 68 may enter the housing 74 via the gas inlet 82, the gas outlet 84 connects the inner volume of housing 74 with the inside of the mask 52'. This can for example be realized by the gas outlet 84 being a tube. Although as indicated as a tube-like arrangement as well, gas inlet 82 may also be realized by a hole-like opening in the housing 74.

Similar to gas supply system 10, the gas supply system 12 is arranged via a support element 66' on the mask 52'.

If the membrane 76 is operated, as will be described later on, ambient air 68 is pumped into the housing 74 via the gas inlet 82. This is indicated by an arrow 86. From the housing 74 the air/gas within the housing 74 is further pumped into the mask 52' via the gas outlet 84. This results in a pressurized gas flow to the mask 52', thereby to the patient interface 32 and accordingly to a subject 50, wearing such a patient interface 32, which is not shown in FIG. 2 for clarity reasons. Also not shown in FIG. 2 are the valves of the gas supply system 12, which are integrated in the housing 74 in this exemplary embodiment.

Figure 3:
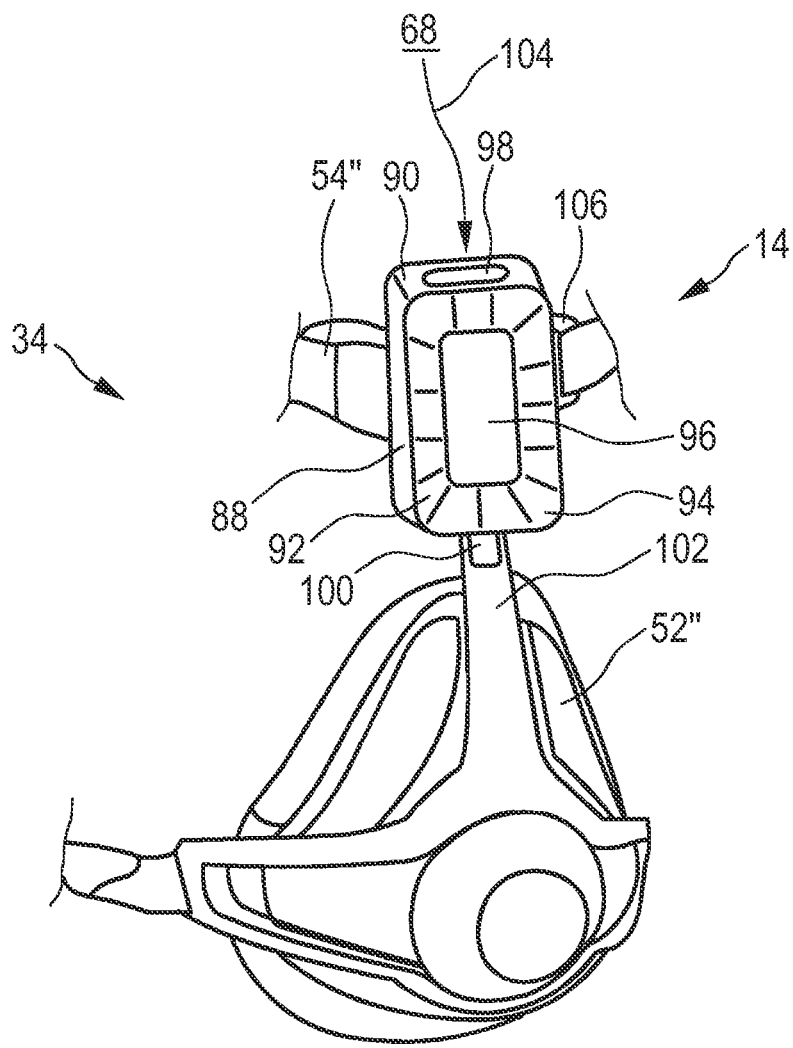
FIG. 3 shows another exemplary embodiment of a gas supply system on a patient interface according to the present invention.

The gas supply system 14 shown in FIG. 3 is part of and accordingly arranged on the patient interface 34. In contrast to the examples of gas supply systems 10 and 12 of FIGS. 1 and 2 the gas supply system 14 is arranged on the head gear 54' of the patient interface 34.

Figure 6:
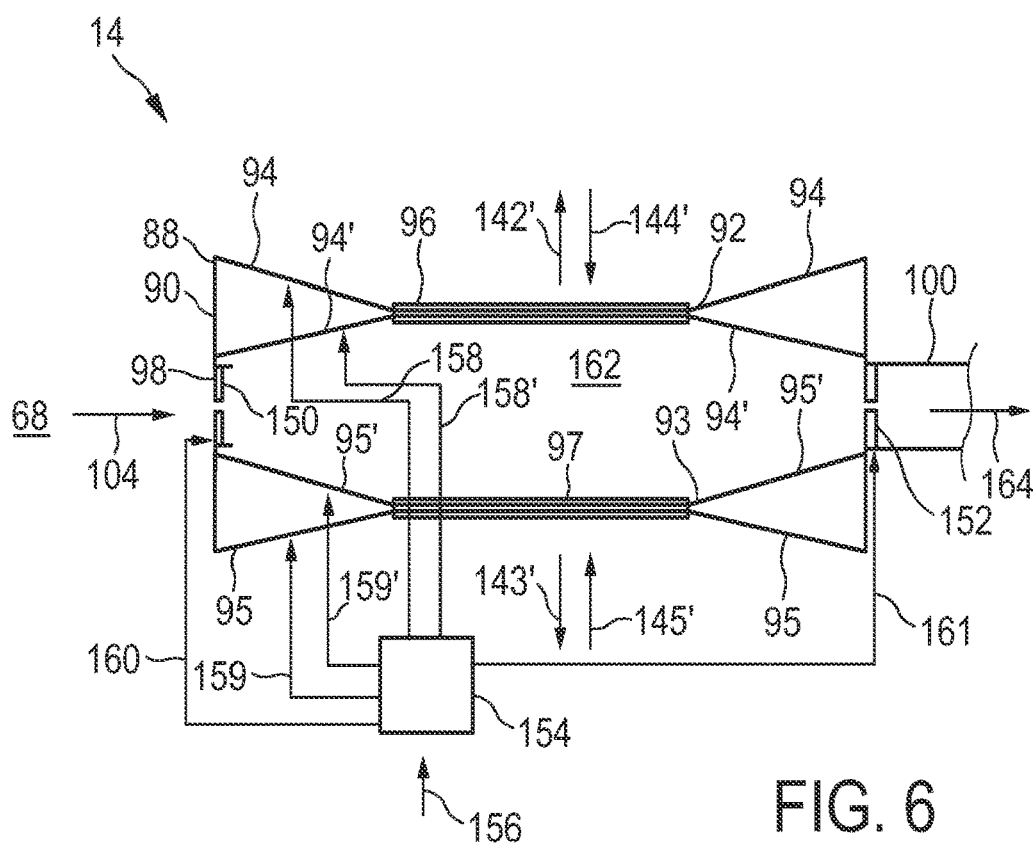
FIG. 6 shows a schematic sectional view through another pump device of a gas supply system according to the present invention.

The gas supply system 14 comprises a housing 90. The housing 90 comprises a membrane 92, in this case also arranged on a distal end of the housing 90, and a proximal membrane 93 (FIG. 6). The membranes 92 and 93 respectively comprise electro-active polymer materials 94 (and 95, FIG. 6) and plates 96 (and 97, FIG. 6). Similar to the embodiment of the gas supply system 12 in FIG. 2, the housing 90 of the gas supply system 14 further comprises a gas inlet 98 and a gas outlet 100. The gas inlet 98 is in this exemplary embodiment designed as an opening within the housing 90. The gas outlet 100 connects the housing 90, that is to say an inner volume 162 (FIG. 6) of the housing 90, with the mask 52". This can be realized by the gas outlet 100 also being a tube. This tube of the gas outlet 100 may end in a mask support 102 which may comprise an inner channel (not shown). This inner channel then ends in the mask 52".

During operation of the membranes 92 and 93 ambient air 68 gets pumped into the housing 90 as it is indicated by an arrow 104. From the inside of the housing 90 the air gets further transferred into the mask 52" via the gas outlet 100 and, for example, via a channel (not shown) of the mask support 102. This results again in a continuous pressurized flow of gas/ambient air 68 via the patient interface 34 to a subject 50, which is not shown for clarity reasons in FIG. 3.

Similar to the exemplary embodiments of gas supply systems 10 and 12 in FIGS. 1 and 2, the gas supply system 14 is separated from a subject 50 via a support element 106, which is in this case arranged on the head gear 54". This support element 106 is also designed of a compressible material resulting in an absorption of any vibrations that may result from the gas supply system 14 during operation.

Figure 4:
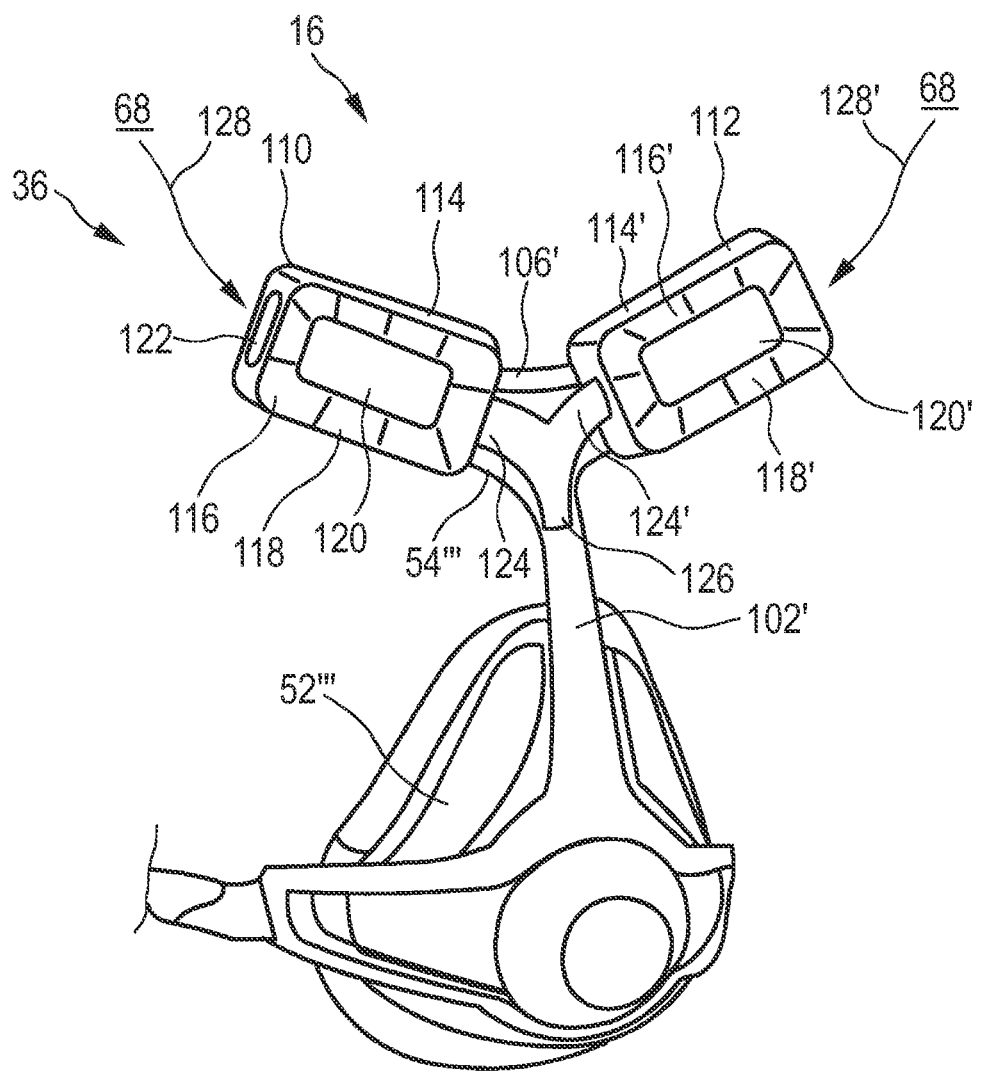
FIG. 4 shows another exemplary embodiment of a gas supply system on a patient interface according to the present invention.

The gas supply system 16 shown in FIG. 4 is arranged on and therefore part of the patient interface 36. The gas supply system comprises two pump devices 110 and 112. Since both pump device 110 and 112 comprise similar or identical features with respect to each other, the same or identical features are designated by the same reference numeral in pump device 112 with respect to pump device 110 only followed by a prime (').

The pump device 110 comprises a housing 114. This housing 114 comprises a membrane 116 arranged on a distal end of the housing 114 and another membrane on the proximal end (not shown). The membrane 116 comprises an electro-active polymer material 118 and a plate 120. The proximal membrane comprises the same configuration. The housing 114 further comprises a gas inlet 122 and a gas outlet 124. The gas inlet 122 is designed as an opening in the housing 114 of the pump device 110. The gas outlet 124 is designed as a tube and is, similar to a embodiment shown in FIG. 3, connected to the mask 52'''. This is realized by combining the gas outlets 124 and 124' of the pump devices 110 and 112 to a combined gas outlet 126. This combined gas outlet 126 is then connected via a channel (not shown) in the mask support 102' of the patient interface 36 to the mask 52'''.

In accordance with the afore-mentioned embodiments a pressurized flow of gas/ambient air 68 into the mask 52''' results from an operation of membranes 116 and 116' of the pump devices 110 and 112 and the respective proximal membranes. Upon this operation ambient air 68 is pumped into the housing 114 or 114' via the gas inlet 122 and 122'. This is indicated by arrows 128 and 128'. From there the air is then transported into the mask 52''' via gas outlets 124 and 124' and the combined gas outlet 126.

In order to reduce any vibration transmitted to the subject 50 wearing such a patient interface 36 a support element 106' is also disposed on the head gear 54''' of the patient interface 36, similar to the exemplary embodiment of the patient interface 34 of FIG. 3.

FIG. 5 shows a schematic sectional view of the gas supply system 10. This sectional view is a cross section through the gas supply system 10 of FIG. 1 resulting from a sagittal cross section with respect to the representation of FIG. 1 wherein the patient interface 30 is worn by a subject 50.

As mentioned before the gas supply system 10 comprises the pump device 55 with the housing 56. Aside from the membrane 58 with the electro-active polymer material 60, plate 62 and valve 64 the gas supply system 10 further comprises the membrane 59 with an electro-active polymer material 61, a plate 63 and a second valve 65. This membrane 59 is arranged opposite from the membrane 58 on the housing 56, as can be seen in FIG. 5. Further, the membranes 58 and 59 are connected via springs, in the present embodiment two springs 128 and 129. These springs 128, 129 are attached to the plates 62 and 63. The purpose of these springs 128, 129 will be explained later on.

Further the gas supply system 10 comprises a controller 130. The controller 130 is connected to a power supply 132 which is indicated by an arrow 134. The controller 130 controls the operation, i.e. actuation, of the membranes 58 and 59. This is realized via controlling an electric field that is applied to the electro-active polymer materials 60 and 61. This is indicated by arrows 136 and 137. Further, the controller 130 may further be designed to receive electric/electronic signals from the electro-active polymer material 60 and 61. By these received electric/electronic data the controller 130 may detect any forces that act on the electro-active polymer material 60 and 61, and thereby on the membranes 58 and 59. These forces can for example be the result of counter pressures due to malfunctions or due to exhaling of the subject 50. This receiving of the signals from the electro-active polymer material 60 and 61 is indicated by further arrows 138 and 139. Based on these data or parameters the controller 130 may adjust the actuation of the membranes 58 and 59 accordingly or submit those data to further control devices or alarm devices.

The controller 130 and power supply 132 may be any suitable controller and any suitable power supply for the desired purpose. Both elements are, for example, arranged in/on the according patient interface 30. The arrangement is preferably such that these parts do not result in any discomfort for a subject 50 wearing the patient interface 30.

The valves 64 and 65 are in this exemplary embodiment designed as passive valves. Such passive valves can be for example designed as duckbill valves. As indicated in the present exemplary representation of FIG. 5, valve 64 is arranged within plate 62 such that it opens towards the inside, that is to say that it allows a stream of, for example, ambient air 68 into the housing 56. The valve 65 on the other hand is arranged in plate 63 such that it only opens to the outside, that is to say only allows air or any other gas that is within the housing 56 to move outside, like into the mask 52. FIG. 5 shows pump device 55 in an unactuated state. Upon actuation of the electro-active polymer material 60 and 61 the membranes, which are fixedly held on the housing 56, move outwardly with respect to an inner closed volume 140. This is indicated by arrows 142 and 143. This outward movement of the membranes 58 and 59 leads to an expansion or increase in size of the closed volume 140. As a result of this expansion of the closed volume 140 the momentary pressure within this volume 140 decreases and falls under the external pressure of the ambient air 68. As a consequence valve 64 opens in order to achieve an equalization of the pressures and allows for ambient air 68 to flow into the volume 140, i.e. into the housing 56.

The springs 128 and 129 mentioned before lead to a bias of the membranes 58 and 59 towards the inside of the housing 56. This means that the aforementioned expansion, i.e. movement of the membranes 58 and 59 in accordance with arrows 142 and 143, is a movement against this bias. After this expansion step of the membranes 58 and 59, the controller 130 stops the actuation of the electro-active polymer materials 60 and 61 such that the membranes 58 and 59 move back, that is to say inwards, due to this bias by springs 128, 129. This is indicated by arrows 144 and 145.

During this inward movement of the membranes 58 and 59 the closed volume 140 gets compressed. As a consequence the pressure within the volume 140, that is to say within housing 56, increases and reaches, at least at some point, a pressure that exceeds the pressure within mask 52. At this point, valve 65 opens, whereas valve 54 is closed, and allows for the gas/air within the housing 56 to flow outside, e.g. into mask 52. This is indicated by arrow 146.

The result of the inward movement is again the state as shown in FIG. 5. Preferably, the springs 128 and 129 are designed such that an inward movement of the membranes 58 and 59 behind this positions shown in FIG. 5 is not possible or at least unfavourable, such that, upon actuation, the membranes 58 and 59 move according to arrows 142 and 143. This prestraining or bias of the membranes 58 and 59 due to springs 128 and 129 leads to a faster and stronger inward movement. Accordingly higher flow rates and pressures can be achieved and a better efficiency of the pump device is the result.

Due to the periodical and fast movement of the membranes 58 and 59 the flow of ambient air 68, that is to say of gas, as indicated by arrows 70 and 146 can be considered as constant and continuous. For this, actuation frequencies of 20 to 200 Hz can be used.

The valves 64 and 65 of the gas supply system 10 are passive and one way valves. In contrast to using passive valves 64 and 65 also valves that may be controlled by a controller can be used. This will be explained in more detail within the context of FIG. 6.

FIG. 6 shows the gas supply system 14 in a sectional view. This sectional view also corresponds to a sagittal cross section considering the patient interface 34 of FIG. 3 is worn by a subject 50 accordingly.

The gas supply system 14 comprises the afore-mentioned pump device 88 with the housing 90. This housing 90 comprises on one side the membrane 92 and on the other opposite side the membrane 93. Similar to the membrane 92 comprising electro-active polymer materials 94 and 94' and a plate 96, the membrane 93 comprises electro-active polymer materials 95 and 95' and a plate 97. In contrast to the design of the gas supply system 10 in FIG. 5, the pump device 88 of gas supply system 14 comprises two electro-active polymer materials 94 and 94' or 95 and 95' in each membrane 92 or 93. The electro-active polymer materials 94 and 94' are arranged such that their respective attachments on the housing 90 are distant from each other, wherein they are joined at the plate 96. The plate 96 thereby preferably holds the electro-active polymer materials 94 and 94' together, in a parallel orientation. This leads to a triangular arrangement of the free lying parts of the electro-active polymer materials 94 and 94', as can be seen in the sectional view of FIG. 6. This applies in the same way to electro-active polymer materials 95 and 95' of the membrane 93 with plate 97.

Also, contrary to the design of the gas supply system 10, the pump device 88 comprises a gas inlet 98 and a gas outlet 100 arranged in the housing 90 of the pump device 88. Gas inlet 98 comprises a valve 150 whereas gas outlet 100 comprises a valve 152. Those valves 150 and 152 are designed as active valves as will be explained in the following.

Similar to the pump device 55 of the gas supply system 10 in FIG. 5, the pump device 88 of gas supply system 14 is also operated by outward and inward movements of the membranes 92 and 93 due to an application of electric fields to the electro-active polymer materials 94, 94' and 95, 95'. The outward movements are indicated by arrows 142' and 143', whereas the inward movements of the membranes 92 and 93 are indicated by arrows 144' and 145'. Wherein these movements are realized via prestrained membranes 58 and 59 of the pump device 55 of FIG. 5 due to the springs 128 and 129 for achieving the inward movement, both movements, inward and outward, in the pump device 88 are avtively controlled by a respective electro-active polymer material. For this, electro-active polymer materials 94 and 94' or 95 and 95' respectively act in an antagonistic fashion, as will be explained in the following.

Although no valves are arranged in the membranes 92 and 93, as it is for example the case for the pump device 55 of FIG. 5, membranes 92 and 93 also have an inner plate 96 and 97, respectively. Aside from making it easier to accomodate a valve within a membrane, like in the membranes 58 and 59 of FIG. 5, those stiff inner plates 96 and 97 aid in the prevention of internal deflection modes. Those deflection modes lead to sound generation and also to a loss of efficiency of the pump device 88. Accordingly inner plates 96 and 97 increase the efficiency of the pump device 88 and also contribute to the comfort of the subject 50 wearing an according patient interface 34. Further, in the example of FIG. 6, the plates 96 and 97 are used to join the electro-active polymer materials 94, 94' and 95, 95', respectively. It goes without saying that aside from the shown examples with inner plates 62 and 63 in FIGS. 5 or 96 and 97 in FIG. 6, also both embodiments lie within the scope of the present invention that comprise flexible inner plates or no plates at all, for example, if the afore-mentioned back drafts can be accepted or avoided due to other material designs or certain control issues.

The gas supply system 14 further comprises a controller 154. The controller 154 is also connected to a power source (not shown) which is indicated by an arrow 156. Controller 154 is designed to control the operation of the membranes 92 and 93 via actuation of the electro-active polymer materials 94, 94' and 95, 95'. This is indicated by arrows 158, 158' and 159, 159'. Further, controller 154 may also control the controllable valves 150 and 152. This is indicated by arrows 160 and 161. Although not shown in FIG. 6, it goes without saying that controller 154 may also receive electric/electronic signals from the membranes 92 and 93 or the valves 150 and 152. This corresponds to the explanations made before within the context of controller 130 of FIG. 5 and is not shown here in more detail for the sake of clarity.

The operation of membranes 92 and 93 via the controller 154 is achieved by a coordinated control of the pairs of electro-active polymer materials 94, 94' and 95, 95'. In the outward movement 142', 143' of the membranes 92 and 93 the controller 154 may actuate the inner lying electro-active polymer materials 94' and 95'. This is indicated by arrows 158' and 159'. At the same time, outer electro-active polymer materials 94 and 95 are not actuated by controller 154. Thereby, the electro-active polymer materials 94' and 95' expand. At the same time, the corresponding antagonists, i.e. electro-active polymer materials 94 and 95, preferably apply a pull force in the direction of arrows 142' and 143' since they are preferably arranged in a strained manner in the housing 90, especially in the state that is shown in FIG. 6. The result is an overall outward movement of membranes 92 and 93 as indicated by arrows 142' and 143'. In this outward movement the controller 154 may either simultaneously or at the same end or at any other suitable time open the valve 150. At the same time, valve 152 is preferably closed. Thereby the pressure of an inner closed volume 162 may be kept at the pressure of the external gas source, in this example ambient air 68. Accordingly ambient air 68 flows into the volume 162 which is indicated by arrow 104. It goes without saying that aside from the here exemplary mentioned ambient air 68 any other gas source, pressurized or unpressurized, may be used accordingly. At the end of the expansion step, i.e. the moving outwards 142', 143', the valve 150 may be closed by the controller 154. After that the inward movement can be started by actuation of the electro-active polymer materials 94 and 95 by the controller 154. This is indicated by arrows 158 and 159. Further, actuation, i.e. expansion, of the electro-active polymer materials 94' and 95' is stopped. This leads to an expansion of the electro-active polymer materials 94 and 95, and a simultaneous pulling due to the contraction of electro-active polymer materials 94' and 95' in the direction of arrows 144' and 145'. Also, the electro-active polymer materials 94' and 95' are preferably arranged in a strained manner as well. The result is the inward movement of membranes 92 and 93 as indicated by arrows 144' and 145'. Thereby the pressure in the closed volume would again increase as already explained within the context of FIG. 5 for the inner volume 140. At some point during this inward movement 144', 145' the controller 154 may open the valve 152. This may be done at the start of the inward movement 144', 145' or at any other suitable time. The result is a flow of gas/air from the volume 162 via the gas outlet 100 as it is indicated by an arrow 164. This flow of gas may then result in the mask 52" of FIG. 3, for example.

The valves 150 and 152 can be any suitable active valve. Example for such valves will be demonstrated later and can also be, for example, valves comprising electro-active polymer materials. The actuation or control of the valves 150 and 152 by the controller 154 is preferably such that a state wherein both valves 150 and 152 are open at the same time is avoided. This increases the efficiency of the pump device 88 since any flows opposite to arrows 104 and 164 are avoided, that is to say, no flow to the ambient air 68 occurs during the inward movement 144', 145', and now flow from via the gas outlet 100, e.g. from a mask 52, occurs during the outward movement 142', 143'.

In the gas supply systems 10 and 14 shown in FIGS. 5 and 6 the movement of the membranes 58 and 59 or 92 and 93 was described such that the respective membranes were designed and controlled to move in opposite directions simultaneously and coordinated. This coordination and movement is controlled by the respective controllers 130 and 154. Due to this movement of a respective membrane 58, 59, 92 or 93 a respective momentum and an according force on the housing 90 or the pump device 88 results in general. Such a force or momentum would usually lead to a vibration of the housing 56 or 90 due to the periodical operation/actuation of the membranes 58 and 59 or 92 and 93. Since the respective membranes pairs 58 and 59 or 92 and 93 are arranged such that their respective movements are coordinated and such that they are oriented against each other, respectively, the sum of the forces resulting due to the actuation of membranes 58 and 59 or 92 and 93, which can also be regarded as the respective arrow pairs 142 and 143, 144 and 145, etc., is lower than each individual force resulting from the respective movements of membranes 58, 59 or 92, 93. In other words, the resulting forces neutralize each other and the sum is preferably reduced to a minimum and even more preferably to zero. As a result the possible vibrations are reduced to a minimum or even more preferably eliminated.

It goes without saying that although the controllers according to the present invention are explicitly and exemplary shown and described within the context of FIGS. 5 and 6 every gas supply system shown and described herein comprises a controller for controlling the actuation of the respective electro-active polymer materials of the respective pump devices, e.g. a controller as shown in FIG. 5 or 6.

The electro-active polymer materials described before, especially within the context of FIGS. 5 and 6, expand upon actuation. This expansion results in the change in size of the at least one closed (inner) volume. Aside from this exemplary arrangement, the opposite way, i.e. actuation by contraction lies also within the scope of the present invention. For this, also DEAPs as electro-active polymer material, as well as other kinds of electro-active polymer materials, like but not limited to ionic polymer-metal composites (IPMC), can be used. One possible and exemplary embodiment could be designed like the pump device shown in FIG. 5. Thereby, the representation of FIG. 5 would show the actuated state. Actuation would occur in the direction of arrows 144 and 145, whereas the following expansion would occur according to arrows 142 and 143 and would result in concave shapes of the corresponding membranes 58, 59. Such an embodiment may work already without any additional biasing means. However, also spring like elements, like springs 128 and 129, may be used as biasing means that are, in contrast to the embodiment of FIG. 5, compressed upon actuation of the electro-active polymer materials and therefore provide a bias in the direction of arrows 142, 143, i.e. outwards. A further non-limiting example of biasing means might be achieved by a honeycomb-shaped structural element that is compressed upon actuation of attached electro-active polymer materials and provides a bias in the opposite direction that results in the desired following expansion.

Similar to such an embodiment based on the pump device of FIG. 5, corresponding embodiments can be achieved on the basis of the design of the pump device shown in FIG. 6. Instead of expanding electro-active polymer materials in the membranes that lead to the movements as described before, also contracting electro-active polymer materials may be used for providing the actuating force. With respect to FIG. 6, contraction of the electro-active polymer material 94 would lead to a movement of the membrane 92 in the direction of arrow 142', whereas the movement in the opposite direction, i.e. in the direction of arrow 144', would be achieved upon actuation, and therefore contraction, of electro-active polymer material 94'. The same principle would apply vice versa to membrane 93 in such an embodiment.

Figure 7:
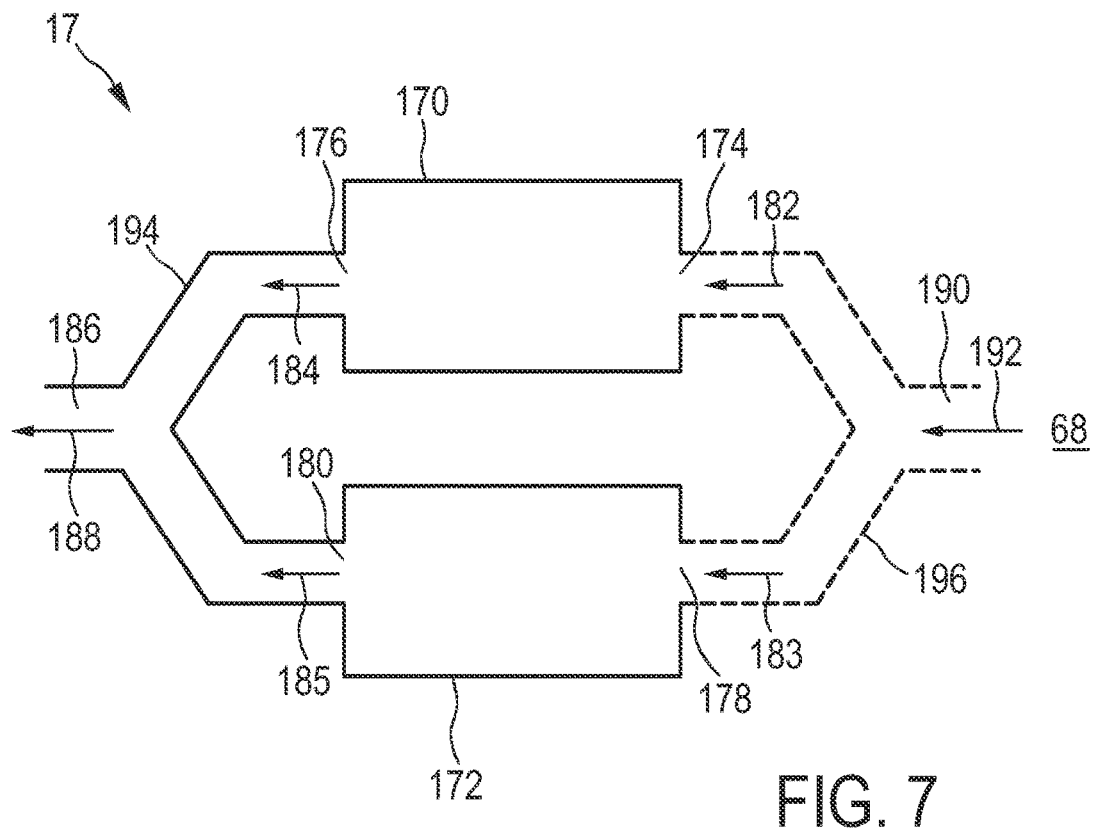
FIG. 7 shows a schematic illustration of a parallel arrangement of pump devices of a gas supply system according to the present invention.

FIG. 7 shows a gas supply system 17. This gas supply system 17 comprises two pump device 170 and 172. Pump device 170 comprises a gas inlet 174 and a gas outlet 176. Pump device 172 comprises a gas inlet 178 and a gas outlet 180. The design of the pump devices 170 and 172 can be any design within the scope of the present invention and is not further explained here. For example, pump device 170 and 172 can be similar or identical to pump device 88 of FIG. 6.

Accordingly during operation of the pump devices 170 and 172 gas can flow into the respective pump devices 170 and 172 via the gas inlets 174 and 178. This is indicated by arrows 182 and 183. With reference to the explanation made before, for example within the context of FIGS. 5 and 6, the result of the operation of the pump devices 170 and 172 is a gas flow out of the pump devices 170 and 172 through the gas outlets 176 and 180. This is indicated by arrows 184 and 185. The output of the pump devices 170 and 172, as respectively indicated by arrows 184 and 185, results in the present example of FIG. 7 in a combined gas outlet 186 and accordingly in a combined gas flow as indicated by arrow 188. The gas flow into the inside of the pump devices 170 and 172 as indicated by arrows 182 and 183 respectively, can be either such that both gas inlets 174 and 178 are connected to a respective gas source or, for example, to ambient air 68. Alternatively, gas inlets 174 and 178 may be combined to a combined gas inlet 190. This gas inlet 190 is illustrated by dashed lines in FIG. 7. Accordingly, the respective gas, e.g. ambient air 68, may flow into the gas supply system 17 via this combined gas inlet 190 as indicated by arrow 192. The aforementioned combined gas outlet 186 and gas inlet 190 may be realized via an appropriately connected system of tubes 194 and 196.

The arrangement of the pump devices 170 and 172 of the gas supply system 17 in FIG. 7 is such that each pump device 170 and 172 may be operated independent from the other. However, a coordinated or concerted operation of the pump devices 170 and 172 is desired in a preferred embodiment. Thereby, a further reduction of vibrations as well as an optimized gas flow can be realized. The shown example of the gas supply system 17 can be regarded as a parallel arrangement of the pump devices 170 and 172 with respect to each other. Such a parallel arrangement affects the overall gas flow as indicated by arrows 192 (or 182 and 183) and arrow 188. Especially the continuity of the flow and also the flow rate may be improved by this parallel arrangement.

Figure 8:
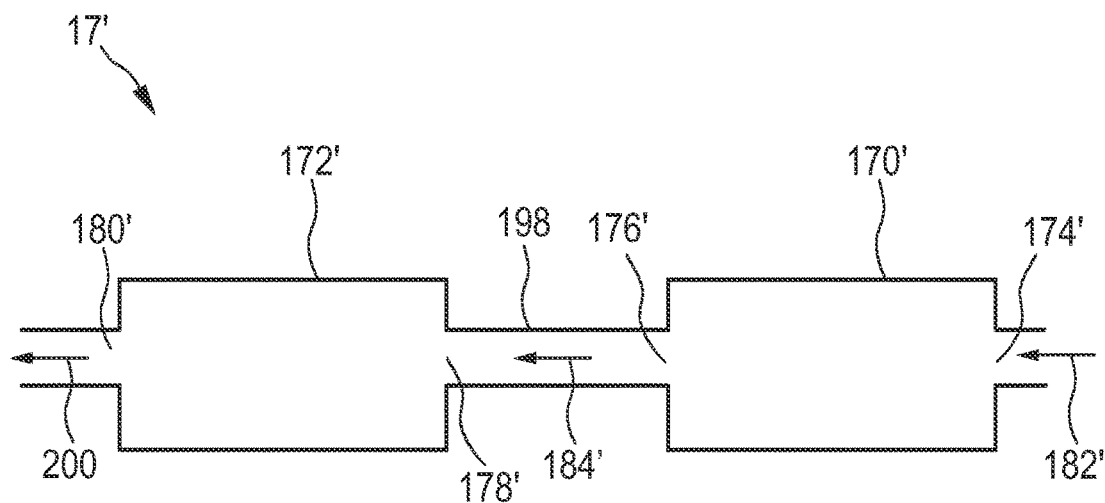
FIG. 8 shows a schematic illustration of a serial arrangement of pump devices of a gas supply systems according to the present invention.

In contrast to the afore-described parallel arrangement of the pump device 170 and 172 in FIG. 7, FIG. 8 shows a serial arrangement of according pump devices 170' and 172'. In this following description of FIG. 8, elements and features similar or identical to the ones shown and described within the context of FIG. 7 are designated by the same reference numeral only differing by a following prime (').

In this serial arrangement the gas outlet 176' of the pump device 170' is connected to the gas inlet 178' of the pump device 172'. This can for example be realized by a direct attachment of the respective pump device 170' and 172' or via a tube 198 as shown in the present exemplary embodiment of the gas supply system 17' of FIG. 8. Similar to FIG. 7, a gas flow into the pump device 170', as indicated by an arrow 182', results in a gas flow out of the pump device 170', which is indicated by an arrow 184'. This gas flow 184' then results in a gas flow inside the pump device 172' via the gas inlet 178'. The result is a gas flow via the gas outlet 180' out of the pump device 172'. This is indicated by an arrow 200.

Such a serial arrangement has the effect that it is thereby possible to optimize and increase the pressure resulting by such a gas supply system 17'. For this, the respective pump devices 170' and 172' comprise preferably valves, as for example described within the context of FIG. 6 and the gas supply system 14 with the pump device 88.

With respect to the parallel arrangement of the gas supply system 17 shown in FIG. 7, such an arrangement is also present in the gas supply system 16 of FIG. 4. The patient interface 36 shown therein also comprises two pump devices 110 and 112 that are arranged parallel with respect to each other. Since both pump devices 110 and 112 comprise a respective independent gas inlet 122 (gas inlet for the pump device 112 not shown in FIG. 4) the set-up can be regarded as the configuration shown in FIG. 7 without the dashed lines. In this respect the gas supply system 17 can be regarded as similar or preferably identical to the gas supply system 16 shown in FIG. 4, or vice versa.

Even though, the respective valves are not shown for every exemplary embodiment of the gas supply systems according to the present invention, every gas supply system comprises at least one valve in order to achieve a continuous flow of pressurized gas/air. The according valves may be chosen from one of the following non-limiting examples.

Figure 9:
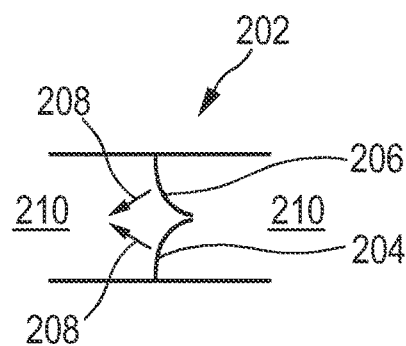
FIG. 9 shows a schematic illustration of an exemplary embodiment of a valve used in the gas supply systems according to the present invention.

FIG. 9 shows a valve 202 having a design of a duckbill valve in a sectional view corresponding to an axis of a flow through this valve. Such a duckbill valve is usually configured as a passive valve wherein the beak-like elements 204 and 206 are prestrained such that they move in a direction as indicated by arrows 208 and result in a closure of the passage 210. A gas flow having a suitable strength or pressure in the direction against these arrows 208 results in a opening of the valve thereby allowing the flow through this valve 202. Contrary to this, a gas flow in the direction corresponding to the arrows 208, i.e. in the opposite direction, is prevented.

Apart from the usual arrangement and design of such a valve 202 as a passive valve, it is also possible and preferred within the scope of the present invention to include elements 204 and 206 of materials that can be actively controlled. Non-limiting examples for such materials are the aforementioned electro-active polymer materials. By using electro-active polymer materials or any other suitable controllable material, the valve can be controlled by a controller, like the controller 154 of FIG. 6. This results in a controlled way of opening and closing the valve 202. Instead of the afore-mentioned prestrain, the control can lead to a closure of the valve 202 by the application of an electrical field leading to a force in a direction corresponding to arrows 208. The contrary operation would be to alter the electric field such that the valve elements 204 and 206 of the valve 202 will move in a direction corresponding to the opposite direction as indicated by arrows 208.

Figure 10A:
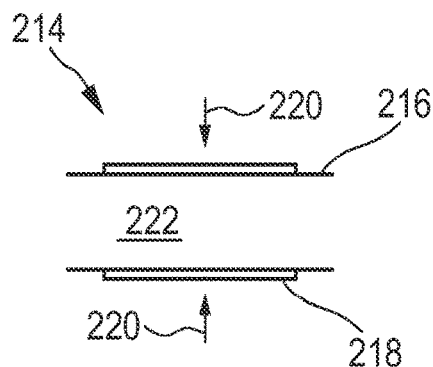
FIGS. 10a and 10b show another exemplary embodiment of a valve used in a gas supply system according to the present invention.
Figure 10B:
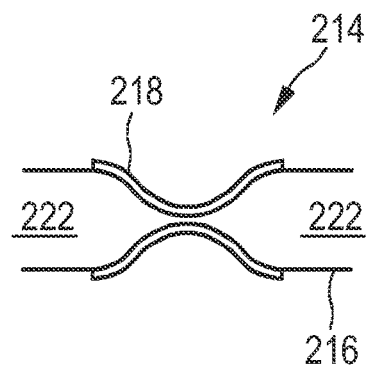

FIGS. 10a and 10b show another example of an active valve 214 in a sectional view corresponding to an axis of the flow through this valve. This active valve 214 basically comprises a tube-like element 216 that itself comprises a controllable element 218. The controllable element 218 may be any suitable element that is designed to and allows for a change in shape. In the present example the controllable element 218 is arranged ring-like around the tube-like element 216. It is in this special example designed for a contraction in a direction as indicated by arrows 220. This results, upon actuation of the controllable element 218, in the configuration as shown in FIG. 10b. Therein, a passage 222 through the tube-like element 216 is closed. Accordingly the valve 214 is in a closed state in the representation in FIG. 10b, and in an open state in the representation of FIG. 10a. The material used for such a controllable element 218 can also be an electro-active polymer material. However, any other suitable shape-shifting material can be used that allows for a compression similar to the one shown in FIG. 10b.

Figure 11A:
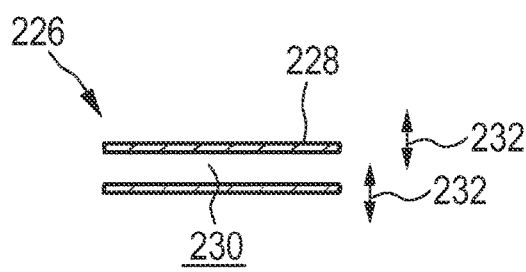
FIGS. 11a and 11b show yet another exemplary embodiment of a valve used in a gas supply system according to the present invention.
Figure 11B:
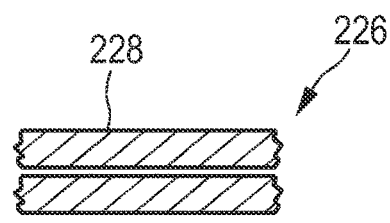

FIGS. 11a and 11b show another exemplary embodiment of a valve 226. This representation also corresponds to a sectional view corresponding to an axis of the flow through this valve. This valve 226 also comprises a tube-like element 228. In this tube-like element 228 a passage 230 exists. The tube-like element 228 comprises a material that, upon actuation, leads to a expansion of the material as indicated by double arrows 232. This expansion 232 basically leads to a compression of the passage 230 in the area of the valve 226. The result of which is shown in FIG. 11b. Accordingly, FIG. 11b shows the closed state of the valve 226, whereas FIG. 11a shows the open state of the valve 226.

Due to the tube-like elements 216 and 228 used in the valves 214 and 226 shown in FIGS. 10a through FIGS. 11b, such valves are also named tube valves.

Figure 12:
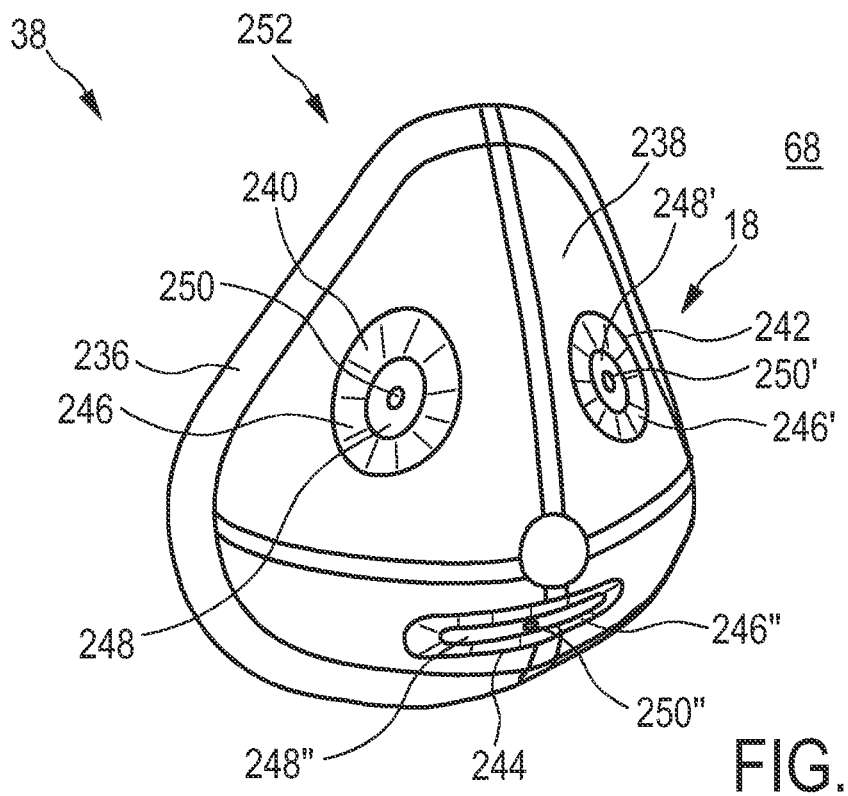
FIG. 12 shows a schematic illustration of another exemplary embodiment of a patient interface according to the present invention.

FIG. 12 shows a further example of a patient interface 38 with a mask 236. The mask 236 comprises a shell 238. In this shell 238 three membranes 240, 242 and 244 are arranged. Similar to the membrane 58 of the pump device 55 in FIG. 5, every membrane 240, 242 and 244 comprises an electro-active polymer material 246, a plate 248 and a valve 250, arranged in the plate 248. Every membrane 240, 242 and 244 is controlled and actuated by a controller (not shown). Membranes 240, 242 and 244 together form a pump device 252.

The working principle of those membranes 240, 242 and 244 is respectively similar to the working principle of the membrane 58 in FIG. 5. Accordingly, an outward movement leads to a flow of gas, in the present example ambient air 68, into an inner closed volume (not shown). This inner closed volume is here realized by the space between the inner surface of shell 238 of the mask 236 and the patient or subject 50, which is not shown in FIG. 12 for clarity reasons. In the next step, an inward movement of the respective membrane 240, 242 and/or 244 leads to a compression of the gas/air within the afore-mentioned inner volume. Due to the periodic repetition of these inward and outward movements of the respective membranes 240, 242 and 244 a flow of ambient air 68 into the afore-mentioned inner volume of the mask 236 occurs.

The afore-mentioned effect of arranging two membranes opposite to each other, for example as shown with the membranes 58 and 59 in FIG. 5, that is to say the reduction or elimination of vibration, is achieved in the present example of the pump device 252 by arranging the membranes 240, 242 and 244 such that the resulting forces of the inward and outward movements are oriented in a way that a sum of the respective forces is lower than each one of the individual forces resulting by the operation of the membrane 240, 242 and/or 244. Preferably, the sum of the respective forces is (almost) zero.

Figure 13:
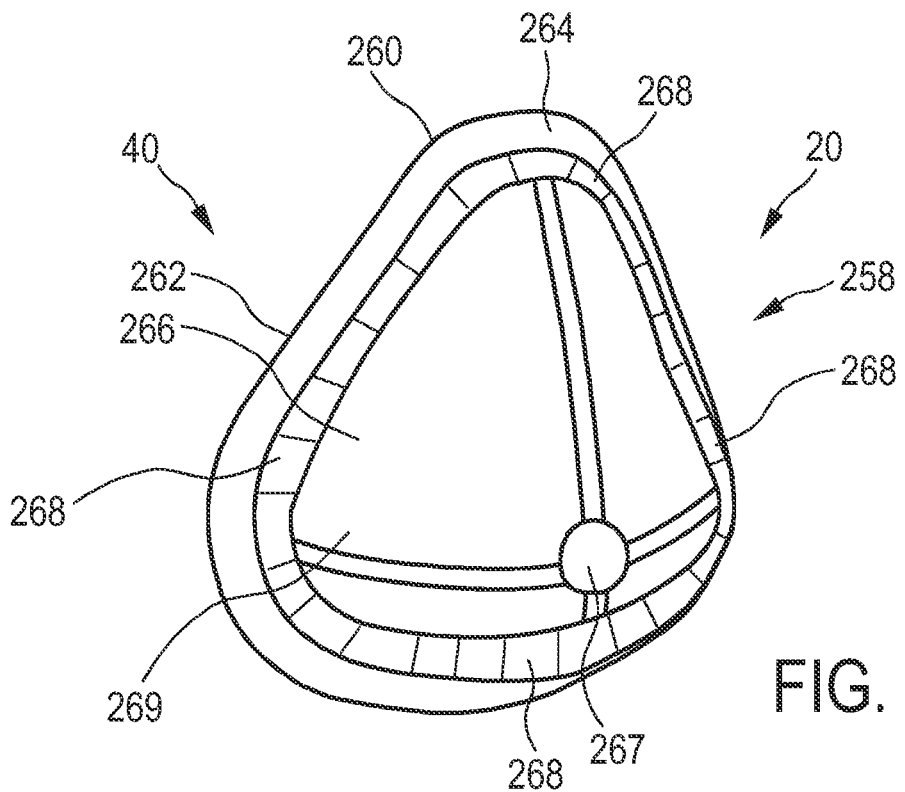
FIG. 13 shows a schematic illustration of another exemplary embodiment of a patient interface according to the present invention.

FIG. 13 shows a further example of a gas supply system 20 on a patient interface 40. The patient interface 40 also comprises a mask 260 having a shell 262. This shell 262 comprises an outer part 264, an inner part 266 and an electro-active polymer material 268 connecting the inner part 266 with the outer part 264. The electro-active polymer material 268 may be arranged in a biased or prestrained way, as for example shown and described within the context of FIG. 5, or with an antagonistic arranged electro-active polymer material (not shown), as for example shown and described within the context of FIG. 6. Upon actuation of this electro-active polymer material(s) 268, the preferably stiff inner part 266 is moved in and outward with respect to an inner volume that results from the shell 262 of the mask 260 and a subject (not shown) wearing the mask 260. With reference to the explanations made before, electro-active polymer material(s) 268 and inner part 266 form a membrane 269.

Due to a valve system 267, which can be realized according to any of the embodiments mentioned before, an according flow of pressurized gas can be provided. Because of the large area of the membrane 269, compared with other embodiments of the present invention, a relatively large flow can be achieved and also lower frequencies may be used. The membrane 269 forms, together with the remaining parts according to the present invention, a pump device 258.

Figure 14:
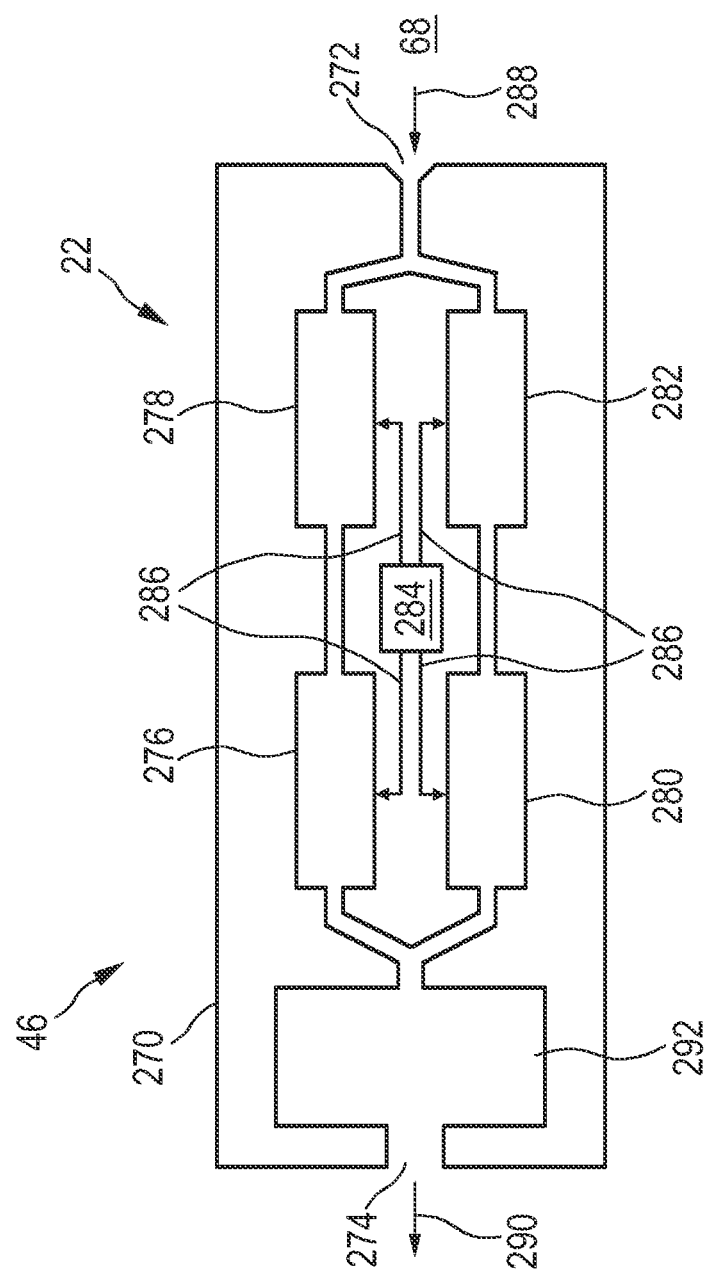
FIG. 14 shows a schematic illustration of a hand-held therapy device according to the present invention.

FIG. 14 shows a schematic representation of a therapy device 46 in a sectional view. This therapy device 46 is designed as a hand-held or portable therapy device 46. "Hand-held" or "portable" device within the context of the present invention is to be understood as a device that is comparably light-weight (e.g. less than 4 kg) and small in size (e.g. a size smaller than two standard books).

The therapy device 46 comprises a housing 270. In the housing 270 a gas inlet 272 is provided. Via this gas inlet 272 gas, e.g. ambient air 68, can be pumped or sucked into the therapy device 46. Further the housing 270 comprises a connector 274. Via this connector 274 a hose (not shown) of a patient interface can be connected to this therapy device 46. As a consequence of this connection, an according patient interface (not shown) can be supplied with a pressurized flow of gas by this therapy device 46.

Within the housing 270 four pump device 276, 278, 280 and 282 are provided. Those pump devices 276, 278, 280 and 282 can be designed (individually) as any pump device according to the present invention. Whereas pump devices 276 and 278 and pump devices 280 and 282 are arranged in series that is to say serial with respect to each other, the group of pump devices 276 and 278 and the group of pump devices 280 and 282 is arranged in parallel with respect to each other. Accordingly, with respect to the working principle and benefits that come with such an arrangement it is referred to the representations and the explanations made within the context of FIGS. 7 and 8.

As can be seen in the exemplary embodiment of FIG. 14, not only two pump devices, as shown in FIGS. 7 and 8 respectively, can be combined to a parallel or serial arrangement, but also parallel and serial arrangements can be combined with each other and more than two pump devices can be used for a set-up. Further, not only two pump devices can be used for a parallel or serial set-up, respectively, but also a serial arrangement with three pump devices or more in one line as well as parallel set-up with three or more devices parallel with respect to each other lies within the scope of the present invention. The choice of the number and of the set-up of the respective pump devices as well as their configuration depends on the needs and possibilities given by the desired purpose. Those needs and possibilities depend on the size of the respective device, that shall accommodate the respective pump devices, as well as on the desired pressure and flow rate that shall be provided by those combinations of pump devices.

The pump devices 276, 278, 280 and 282 are controlled by a controller 284, which is indicated by arrows 286. Regarding the working principle and the control of the respective pump devices 276 through 282 it is here again referred to the explanations made before, for example within the context of FIGS. 7 and 8 or within the context of FIGS. 5 and 6.

The result of the operation of the respective pump device 276, 278, 280 and 282 is a flow of gas, in this case ambient air 68, through the gas inlet 272 into the therapy device 46. This is indicated by an arrow 288. Further, a continuous and controlled flow of pressurized gas is provided via the connector 274 to a desired destination device, for example a patient interface (not shown). This is indicated by arrow 290. In order to achieve a more constant flow and in order to flatten out pressure variations, the therapy device 46 further comprises a buffer volume 292. This buffer volume 292 may also act as a buffer such that the pump devices 276, 278, 280, 282 do not have to be adjusted in their operation because of possible high fluctuations in flow demand by a subject/patient, but can work in a continuous way.

By using those pump devices 276 through 282, that also comprise a membrane in accordance with the present invention, that is to say with an electro-active polymer material for actuation, an overall therapy device 46 can be built with desired features. Those features are, as mentioned before, a smaller and flexible size and a reduced weight while keeping the pressure and flow rate of the provided flow 290 at a level that is also provided by classic therapy devices. The therapy device 46 is therefore ideal for travel purposes or for any purpose where the user of such a therapy device 46, e.g. subject 50, often sleeps in different places and requires an according therapy device.

Together, the pump devices 276 through 282, the controller 284, the buffer volume 292 and valves according to the present invention (not shown) form the gas supply system 22.

Figure 15:
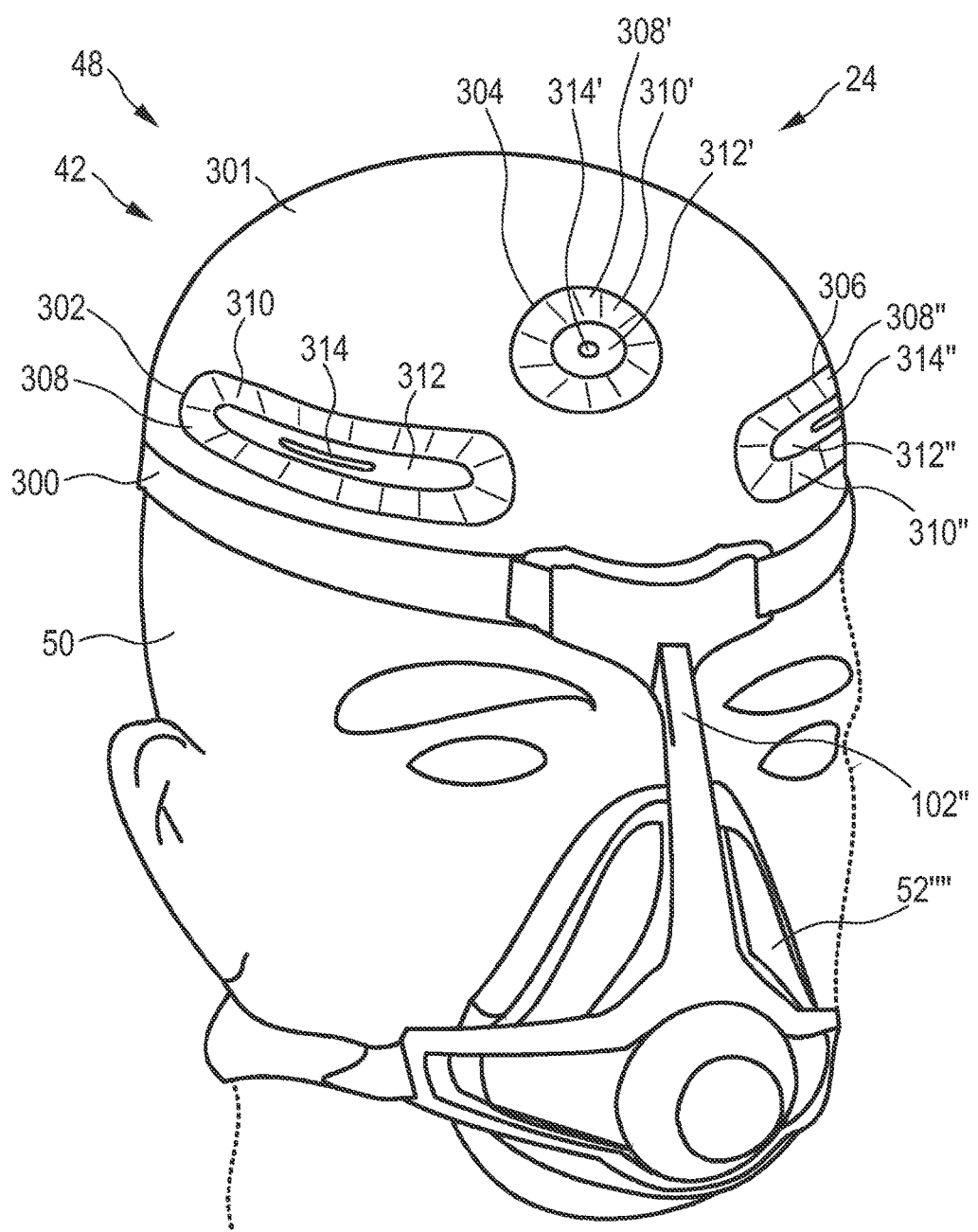
FIG. 15 shows a schematic illustration of another exemplary embodiment of a patient interface according to the present invention.

FIG. 15 shows a patient interface 42 worn by the subject 50. The patient interface 42 comprises a mask 52'''', a headgear 300 and a gas supply system 24. The headgear 300 comprises a head cap 301. This head cap 301 is worn by the subject 50 in order to achieve an optimal fit of the mask 52'' for an optimal supply of a pressurized flow of gas/air to subject 50. The gas supply system 24 comprises in this exemplary embodiment three pump devices 302, 304 and 306. Each pump device 302, 304, 306 comprises a membrane 308 with an electro-active polymer material 310 and a plate 312. In the plate 312, a valve 314 is arranged. The design of the present pump devices 302, 304 and 306 is similar to the one shown and described within the context of FIGS. 5 and 12. The pressurized flow of gas/air provided by these pump devices 302, 304 and 306 is directed into the mask 52'''' via channels and tubing (not shown) within the head cap 301 and the mask support 102'' of the headgear 300. Also, the gas supply system 24 comprises a controller (not shown) for controlling the pump devices 302, 304 and 306 in accordance with the exemplary embodiments mentioned before.

The pump devices 302, 304 and 306 are arranged in/at the head cap 301. This arrangement allows for larger and/or more pump devices such that the provision of a larger flow is possible, preferably while simultaneously using lowing actuating frequencies for the membranes of the used pump devices. Due to the flexibility in shape and form of the membranes 308 with the electro-active polymer materials 310 as actuators, the pump devices 302, 304, 306 can be easily accommodated to the rounded form of the head cap 301. Preferably, also a thin form of the pump devices 302, 304, 306 may be achieved such that the head cap 301 does not result in a thick shell that has to be worn by the subject 50, but as a relatively thin head cap 301 that does not disturb the subject 50 during sleep and is comfortable to wear. Aside from the shown exemplary embodiment with the three pump devices 302, 304 and 306, any suitable number and/or form of pump devices with the according membranes may be used to achieve the desired results with respect to pressure and flow rate, i.e. pump efficiency, and comfort for the subject 50. Further, a preferred distributed arrangement of the used pump devices at/in the head cap 301 leads to the aforementioned reduction of forces that result from the operation of those pump devices. Similar to the exemplary embodiments mentioned before, the overall force that results and is felt by the subject 50 is lower than each of the individual forces, preferably less the 10% of each individual force, and more preferably cancelled out.

As mentioned before, the use of a head cap, like head cap 301, allows also for larger and/or more pump devices. Whereas the focus of the exemplary embodiment of head cap 301 lies on larger and more pump devices, it goes without saying that also head caps with just one large pump device lie within the scope of the present invention. Such a pump device would then be designed similar to the pump device 258 of the gas supply system 20 in FIG. 13, wherein the larger membrane 269 in form of the inner part 266 and the electro-active polymer material 268 is used. This means that a membrane with an area comparable to the embodiment of FIG. 13, or an even larger membrane, can be used on a head cap according to the present invention. This leads to frequencies for actuation of the membrane that are even lower and may also provide the pressurized gas flow more efficiently.

Although shown this way in the exemplary embodiment of FIG. 15, the head cap 301, or any other head cap according to the present invention, does not need to cover the whole head. Therefore, also head caps that are only as large as necessary to accommodate the pump device(s) lie within the scope of the present invention.

Although, the head cap 301 with the gas supply system 24 is described as a part of the patient interface 42 in the present exemplary embodiment, it goes without saying that the head cap 301 can also be regarded as a part of the gas supply system 24 itself, according to the present invention. Such a gas supply system 24 is independent of a certain patient interface, like patient interface 42, and can be used and applied as a separate device to existing patient interfaces or masks in general.

Accordingly, the head cap 301, or any other head cap according to the present invention, can be regarded as a therapy device 48 according to the present invention. Aside from arranging such a therapy device according to the present invention as a separate (handheld) device, as shown and described within the context of FIG. 14, or as a head cap, as shown and described before within the context of FIG. 15, other forms of such therapy devices are possible, like but not limiting to portable therapy devices that can be attached to the patient via one or more straps, e.g. to the patient's chest. Such an exemplary therapy device may be configured relatively thin and may also have a shape that is adapted to the body part of the patient where it is attached to. These thin and adapted designs are once more possible due to the flexibility in design of the membranes and the according pump devices and the resulting gas supply systems according to the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A gas supply system for a patient interface for supplying a flow of pressurized gas to a subject, with:
at least one pump device, comprising:
at least two membranes, each membrane comprising at least one electro-active polymer material, and
at least one valve; and
a controller, for controlling the at least one pump device, wherein the at least one pump device comprises at least one closed volume, and wherein the membranes are arranged on opposite sides of the closed volume such that they are in operative communication with the at least one closed volume and are further designed for altering the volume of the at least one closed volume by moving toward or away from each other based on actuation by the electro-active polymer material in a periodic way resulting in a flow of pressurized gas from the at least one closed volume.

2. The gas supply system of claim 1, with at least two pump devices.

3. The gas supply system of claim 1, wherein each membrane is configured to generate a force due to its movement upon actuation, wherein the membranes are arranged in the gas supply system such that the sum of the forces of the membranes is lower than each individual force of the membranes.

4. The gas supply system of claim 1, wherein the at least one valve is an active valve.

5. The gas supply system of claim 1, wherein the at least one valve is actuated by an electro-active polymer material.

6. The gas supply system of claim 4, wherein an actuation of the at least one valve is synchronized with the actuation of the at least two membranes.

7. The gas supply system of claim 1, wherein the at least one valve is arranged in one of the at least two membranes.

8. The gas supply system of claim 1, wherein the at least one pump device comprises:
at least one inlet valve, and
at least one outlet valve.

9. A patient interface for supplying a flow of pressurized gas to a subject, with:
an interfacing portion that is configured to contact the subject, and
the gas supply system according to claim 1.

10. The patient interface of claim 9, wherein the gas supply system is an integral part of the patient interface.

11. The patient interface of claim 9, wherein the interfacing portion comprises a mask having an outer shell, and wherein the at least two membranes of the pump device are arranged in the shell of the mask.

12. Therapy device for providing a controlled flow of pressurized gas to a patient interface, with a gas supply system according to claim 1.

13. The gas supply system of claim 1, wherein the at least two membranes are coupled together by a spring element extending between the at least two elements.

* * * * *